United States Patent [19]

Naumann et al.

[11] Patent Number: 4,699,922

[45] Date of Patent: Oct. 13, 1987

[54] TETRAMETHYLCYCLOPROPANECARBOXYLATES

[75] Inventors: Klaus Naumann, Leverkusen; Rudolf Braden, Odenthal; Wolfgang Behrenz, Overath-Steinenbrueck; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 873,746

[22] Filed: Jun. 12, 1986

[30] Foreign Application Priority Data

Jun. 25, 1985 [DE] Fed. Rep. of Germany ....... 3522623

[51] Int. Cl.⁴ .................. C07C 69/74; A01N 53/00
[52] U.S. Cl. ................................. 514/531; 560/124
[58] Field of Search ................. 560/124; 514/531

[56] References Cited

U.S. PATENT DOCUMENTS 4,370,346 1/1983 Punja ..................................... 560/124

FOREIGN PATENT DOCUMENTS 0031199 7/1981 European Pat. Off. .
0060617 9/1982 European Pat. Off. .
2097384 11/1982 United Kingdom ................ 560/124

OTHER PUBLICATIONS

Elliott, Chem. Soc. Rev., 1, pp. 473-505, (1978).

Primary Examiner—Michael L. Shippen
Attorney, Agent, or Firm—Sprung Horn Kramer & Woods

[57] ABSTRACT

Pesticidal compositions useful in protecting plants and also in the hygiene field are disclosed. The new tetramethylcyclopropanecarboxylates have the formula

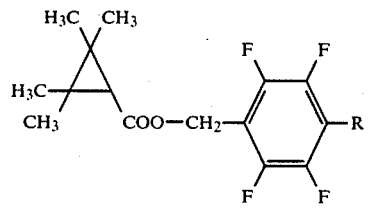

where R represents mercapto, methylthio, alkylsulphenyl or alkylsulphonyl.

4 Claims, No Drawings

TETRAMETHYLCYCLOPROPANECARBOXYLATES

The present invention relates to new tetramethylcyclopropanecarboxylates, a process for their preparation, their use as plant protection agents, in particular as insecticides and acaricides, and new intermediate products for their preparation and processes for their preparation.

It has already been disclosed that cyclopropanecarboxylates having a similar structure (for example in EP-A 0 060 617) can be used as insecticides. However, these possess substantially less pronounced activity than the compounds according to the invention.

New tetramethylcyclopropanecarboxylates of the formula

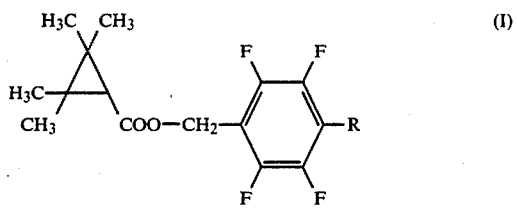

in which
R represents mercapto, methylthio, alkylsulphinyl or alkylsulphonyl, have been found. The alkylsulphinyl group R preferably contains 1 to 6 carbon atoms. The alkylsulphonyl group R also preferably contains 1 to 6 carbon atoms.

The new tetramethylcyclopropanecarboxylates of the formula I

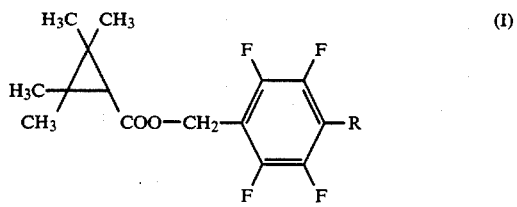

in which
R represents mercapto, methylthio, alkylsulphinyl, or alkylsulphonyl, are obtained when tetramethylcyclopropanecarboxylic acid or its reactive derivative of the formula II

in which
$Z_1$ denotes halogen, preferably chlorine, or OH,
is reacted with an alcohol or its reactive derivative of the formula III

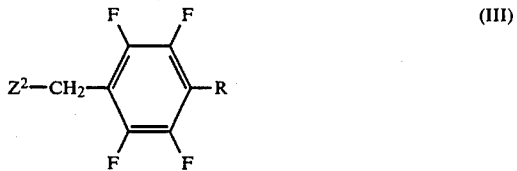

in which
R has the meaning given above and $Z^2$ represents OH, Cl or Br, if appropriate in the presence of solvents, acid acceptors and/or phase-transfer catalysts.

The reaction of the compounds (II) with those of the formula (III) is preferably carried out without the presence of solvents. The alcohols or reactive alcohol derivatives of the formula III

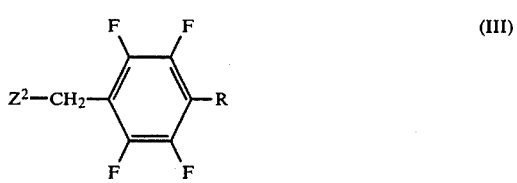

wherein
R and $Z^2$ have the meanings given above, are prepared by reacting pentafluorobenzyl alcohol or its derivatives of the formula (IV)

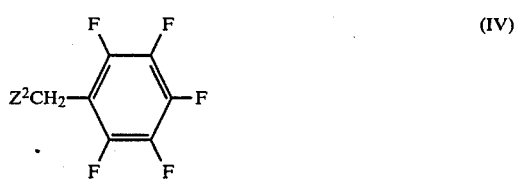

wherein
$Z^2$ represents OH, Cl or Br,
with compounds of the formula (V)

$$R-H \qquad (V)$$

wherein
R represents mercapto, methylthio, alkylsulphinyl or alkylsulphonyl,
if appropriate in the presence of acid acceptors.

Surprisingly, the tetramethylcyclopropanecarboxylates according to the invention of the formula (I) have a substantially more powerful insecticidal action than the prior art compounds according to EP-A 0 060 617.

The following may be mentioned as compounds of the general formula I

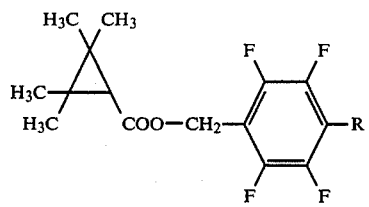

wherein

R has the following meanings: $SCH_3$, $SH$, $SOCH_3$, $SOC_2H_5$, $SO_2CH_3$, $SO_2C_2H_5$, $SO\text{-}nC_3H_7$, $SO_2nC_3H_7$.

If, for example, tetramethylcyclopropanecarbonyl chloride and 2,3,5,6-tetrafluoro-4-methylmercaptobenzyl alcohol are used as starting components, the course of the reaction can be represented by the following equation:

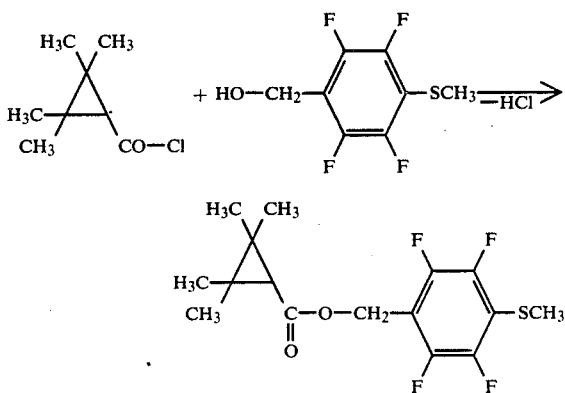

Benzyl alcohols or their reactive derivatives of the formula (III) are employed as starting materials. The chlorides are preferably used as reactive derivatives.

The following may be mentioned individually as examples of the compounds of the formula III which are to be used as starting materials:
4-Mercapto-2,3,5,6-tetrafluorobenzyl alcohol
4-Methylmercapto-2,3,5,6-tetrafluorobenzyl alcohol
4-Methylsulphinyl-2,3,5,6-tetrafluorobenzyl alcohol
4-Ethylsulphinyl-2,3,5,6-tetrafluorobenzyl alcohol
4-Methylsulphonyl-2,3,5,6-tetrafluorobenzyl alcohol
4-Ethylsulphonyl-2,3,5,6-tetrafluorobenzyl alcohol.

The reaction of the acids or reactive derivatives of the acids of the formula (II) with the alcohols or the reactive derivatives of the alcohols (III) is preferably carried out in the absence of solvents. In particular, the acyl chlorides (formula II, $Z_1=Cl$) are reacted in this way, the mixture being heated in this case until the evolution of hydrogen chloride is complete. It is of course also possible to react other acyl halides, such as, for example, acyl bromides, in this manner.

The reaction products are worked up in general by distillation.

However, it is also possible to use, for example, all conventional acid-binding agents as acid acceptors for the preparation of the compounds according to the invention, of the formula I, according to 1. (above) from carboxylic acids or carboxylic acid halides of the formula II and alcohols or chlorides or bromides of the formula III.

Alkali metal hydroxides, alkali metal carbonates and alkali metal alcoholates, such as potassium hydroxide, sodium hydroxide, sodium methylate, potassium carbonate or sodium ethylate, and aliphatic, aromatic or heterocyclic amines, for example triethylamine, trimethylamine, dimethylaniline, dimethylbenzylamine and pyridine, have proved particularly useful.

The reaction temperature for the reaction of compounds (II) with compounds (III) can be varied within a relatively wide range. In general, the reaction of the acyl halides with alcohols is carried out at between 0° and 100° C., preferably at 15° to 40° C., and the reaction of the carboxylic acid with the halides is carried out at between 50° and 150° C., preferably at 80° to 120° C. In the latter case, the reaction is preferably carried out in the presence of a catalyst.

Suitable catalysts are all so-called phase-transfer catalysts, such as, for example, crown ethers or quaternary ammonium or phosphonium salts. Quaternary ammonium salts, such as, for example, tetrabutylammonium chloride, tetrabutylammonium bromide, benzyltriethylammonium chloride or methyltrioctylammonium chloride, are preferred.

The reaction is generally allowed to take place under atmospheric pressure. The process for the preparation of the compounds according to the invention is preferably carried out without using solvents. Of course, the reaction can also be carried out in the presence of suitable solvents and diluents. Suitable solvents and diluents are all inert organic solvents. These include, in particular, aliphatic and aromatic, optionally chlorinated hydrocarbons, such as benzene, toluene, xylene, benzine, methylene chloride, chloroform, dichloroethane, chlorobenzene or o-dichlorobenzene, and ethers, for example, diethyl, diisopropyl or dibutyl ether, as well as nitriles, such as acetonitrile and propionitrile.

Another preferred method of preparation is the reaction of the alkali metal salts of the acids with appropriate benzyl halides of the formula III ($Z^2=Cl$, Br) in the presence of, for example, catalytic amounts of pentamethylethylenetriamines or similar amines and, for example, in acetonitrile, as described in, for example, Synthesis 1975, 805.

In carrying out the process, the starting components are preferably employed in equimolar amounts. The reaction components are combined, if appropriate, in one of the stated solvents, and generally stirred at elevated temperature, after the addition of the acid acceptor and, if appropriate, the catalyst, for one or more hours to complete the reaction. Thereafter, the reaction mixture is poured into water, and the organic phase is separated off and washed neutral with water. After the mixture has been dried, the solvent is distilled off in vacuo.

Another method for the preparation of 2,2,3,3-tetramethylcyclopropanecarbonic acid methylmercaptobenzylester is characterised therein that 2,2,3,3-tetramethylcyclopropanecarbonicacid-pentafluorobenzylester is reacted with an alkalimetal mercaptide, preferably with sodium methylmercaptide in an organic solvent, preferably under inert gas (especially nitrogen gas) and the organic phase is thereafter removed by means of distillation.

The active compounds are well tolerated by plants, have a favourable level of toxicity to warm-blooded animals, and are suitable for combating animal pests, especially insects and Arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus Spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, malacosoma neustria, Euproctis chrysorrhoea,* Lymantria spp., *BucCulatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigation coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation-products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention are used in the form of their commercially available formulations and/or in the use forms prepared from these formulations.

The active compound content of the use forms prepared from the commercially available formulations can vary within wide limits. The active compound concentration of the use forms can be from 0.0000001 to 100% by weight of active compound, preferably between 0.01 and 10% by weight.

The compounds are employed in a customary manner appropriate for the use forms.

When used against hygiene pests and pests of stored products, the active compounds are distinguished by an excellent residual action on wood and clay as well as good stability to alkali on limed substrates.

The active compounds according to the invention are used in a known manner in the veterinary sector, such as by dermal application, for example in the form of dipping, spraying, pouring on and spotting on, and dusting.

EXAMPLE A

LD$_{100}$ test

Test animals: *Leucophea maderae*
Solvent: acetone 2 parts by weight of active compound are taken up in 1,000 parts by volume of the solvent. The solution thus obtained is diluted with further solvent to the desired concentrations.

2.5 ml of the solution of active compound are pipetted into a Petri dish. On the bottom of the Petri dish there is a filter paper with a diameter of about 9.5 cm. The Petri dish remains uncovered until the solvent has completely evaporated. The amount of active compound per m$^2$ of filter paper varies with the concentration of the solution of active compound. 5 test animals are then placed in the Petri dish and the dish is covered with a glass lid.

The condition of the test animals is checked 3 days after the commencement of the experiments. The destruction in % is determined.

In this test, for example, the compound from preparation example 1 which has the formula

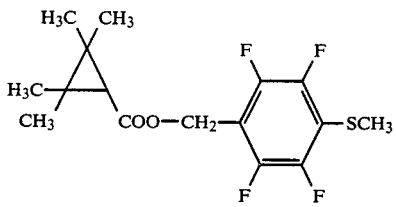

showed a superior activity compared to the prior art.

EXAMPLE B

LT$_{100}$ test for Diptera

Test animal: *Musca domestica*, 2. *Aedes aegypti*
Solvent: acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m$^2$ of filter paper varies, depending on the concentration of the active compound solution. About 25 test animals are then introduced into the Petri dish, and the dish is covered with a glass lid.

The condition of the test animals is checked continuously. The time required for a 100% knock-down effect is determined.

In this test, for example, the compound from preparation example 1 which has the formula

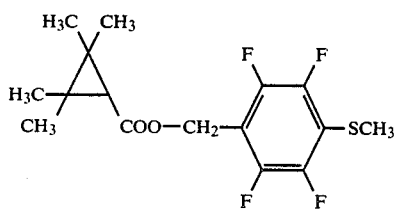

had a superior activity compared to the prior art.

EXAMPLE C

Nephotettix test

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice Leafhopper (*Nephotettix cincticeps*) as long as the seedlings are still moist.

After the desired time, the destruction in % is determined. 100% means that all leafhoppers have been killed; 0% means that no leafhoppers have been killed.

In this test, for example, the compound of preparation example 1 which has the formula

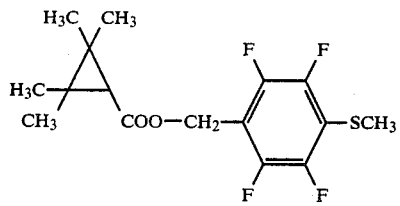

showed a superior activity compared to the prior art.

EXAMPLE D

Tetranychus test (resistant)

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the compound from preparation example 1 which has the formula

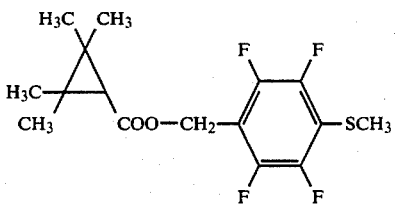

showed a superior activity compared to the prior art.

EXAMPLE E

Critical concentration test/soil insects

Test insect: *Phorbia antiqua* grubs (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with the soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compound from preparation example 1 which has the formula

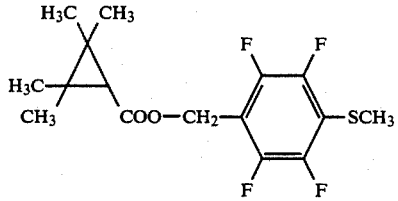

showed a superior activity compared to the prior art.

EXAMPLE F

Critical concentration test/soil insects

Test insect: *Diabrotica balteate*-larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with the soil. The concentration of the active compound in the preparation is of practically no importance, only the amount by weight of active compound per unit volume of soil, which is given in ppm (=mg/liter) being decisive. The soil is filled into 0.5 l pots and the pots are left to stand at 20° C.

Immediately after this, 6 germinated maize kernels are placed in each pot. After 2 days, the appropriate test insects are placed in the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compound from preparation example 1 which has the formula

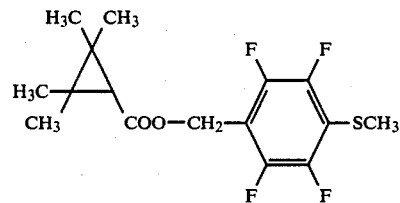

showed a superior activity compared to the prior art.

EXAMPLE 1

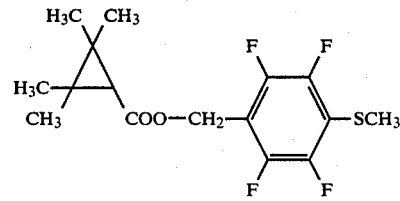

0.1 mol (16 g) of tetramethylcyclopropanecarbonyl chloride and 0.1 mol (22.6 g) of 2,3,5,6-tetrafluoro-4-methylmercaptobenzylalcohol were heated together to 50° to 70° C. in the absence of a solvent until the evolution of hydrogen chloride had ceased. The product was then distilled in vacuo. 39 g of a compound of the above formula were obtained (b.p. 0.1: 120° C.)

IR spectrum: 2950, 1730, 1640, 1470, 1420, 1330, 1270, 1190, 1140, 1120, 1070, 1050, 910, 870, Explanation: Here and in the boiling point below, the expression "b.p. 0.1" means at 0.1 mm mercury column.

The following compounds were prepared in an analogous manner:

General formula:

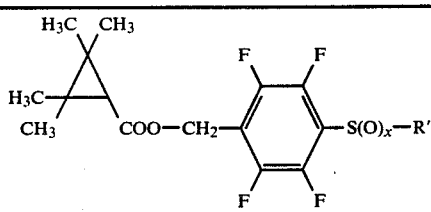

| Example No. | R' | X | Physical data |
| --- | --- | --- | --- |
| 2 | H | 0 | B.p. 0.1 110° C. |
| 3 | CH₃ | 1 | B.p. 0.1 130° C. |

EXAMPLE 4

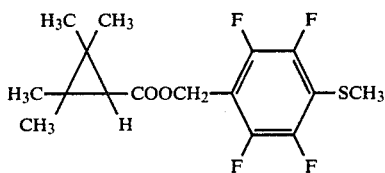

0.1 mol of sodiummethylmercaptide are added dropwise at 10° C. under nitrogen to 0.1 mol of 2,2,3,3-tetramethylcyclopropanecarbonic acid-pentafluorobenzylester in 150 ml of methylenechloride. After having reached the neutral point, the organic phase is distilled in vacuo (bulb tube, kiln temperature: 230° C., pressure: 0.05 mm). According to the NMR spectrum the pure compound 2,2,3,3-tetramethylcyclopropanecarbonicacid-tetrafluoro-4-methylmercaptobenzylester having the above identified formula is obtained.

EXAMPLE 5

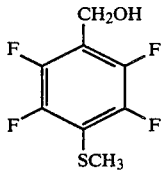

In a stirring apparatus comprising a 250 ml three-necked flask and equipped with a thermometer, condenser and a cooling bath, 100 ml of isopropanol are initially introduced at 0° C., 5 g of methylmercaptan are then passed in and 4 g of powdered sodium hydroxide are added. Thereafter, 20 g of pentafluorobenzyl alcohol are added dropwise in the course of 15 minutes at 0° C. via a heatable dropping funnel. The mixture is then slowly heated to the reflux temperature (83°–84° C.) and stirred at this temperature for one hour. The mixture is cooled and poured onto ice water. The greasy crystals formed are taken up in methylene chloride.

The two phases are then separated, and the organic phase is dried over sodium sulphate and distilled over a column. 16.6 g of 2,3,5-tetrafluoro-4-methylmercaptobenzyl alcohol are obtained (b.p. 16 mbar: 145°–146° C.).

It will be understood that the specification and examples are illustrative but not limitative of the present invention and that other embodiments within the spirit and scope of the invention will suggest themselves to those skilled in the art.

What is claimed is:

1. A tetramethylcyclopropanecarboxylate of the formula

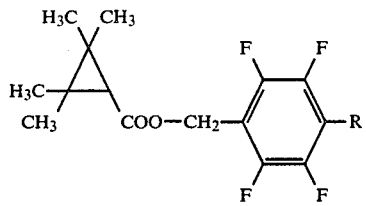

in which
R represents mercapto or methylthio.

2. A tetramethylcyclopropanecarboxylate according to claim 1, wherein

R=methylthio.

3. An insecticidal or accaricidal composition comprising at least one tetramethylcyclopropanecarboxylate according to claim 1 and a suitable extender.

4. A method for combating insects or acarids comprising applying to said insects or acarids or the habitat thereof an insecticidal or acaricidal effective amount of a tetramethylcyclopropanecarboxylate according to claim 1.

* * * * *